(12) United States Patent
McGuire

(10) Patent No.: US 9,687,829 B2
(45) Date of Patent: Jun. 27, 2017

(54) CATALYST FOR PYROLYSIS OF FEEDSTOCK

(71) Applicant: BASF Corporation, Florham Park, NJ (US)

(72) Inventor: Robert McGuire, Nanuet, NY (US)

(73) Assignee: BASF CORPORATION, Florham Park, NJ (US)

( * ) Notice: Subject to any disclaimer, the term of this patent is extended or adjusted under 35 U.S.C. 154(b) by 37 days.

(21) Appl. No.: 14/616,028

(22) Filed: Feb. 6, 2015

(65) Prior Publication Data

US 2015/0224485 A1 Aug. 13, 2015

Related U.S. Application Data

(60) Provisional application No. 61/937,001, filed on Feb. 7, 2014.

(51) Int. Cl.
| | | |
|---|---|---|
| *B01J 23/00* | (2006.01) | |
| *B01J 20/18* | (2006.01) | |
| (Continued) | | |

(52) U.S. Cl.
CPC ........... *B01J 29/80* (2013.01); *B01J 23/6567* (2013.01); *B01J 29/061* (2013.01); *B01J 35/0006* (2013.01); *B01J 37/04* (2013.01); *C01B 3/16* (2013.01); *C07C 1/20* (2013.01); *C07C 27/00* (2013.01); *C07C 37/52* (2013.01); *C07C 41/01* (2013.01); *C10G 3/49* (2013.01); *B01J 21/06* (2013.01); *B01J 21/08* (2013.01); *B01J 23/16* (2013.01); *B01J 23/24* (2013.01); *B01J 23/42* (2013.01); *B01J 23/755* (2013.01); *B01J 29/084* (2013.01); *B01J 29/166* (2013.01); *B01J 29/40* (2013.01); *B01J 29/48* (2013.01); *B01J 29/87* (2013.01); *B01J 35/08* (2013.01); *B01J 37/0205* (2013.01); *B01J 2229/42* (2013.01); *C07C 2521/04* (2013.01); *C07C 2523/28* (2013.01); *C07C 2523/36* (2013.01);

(Continued)

(58) Field of Classification Search
CPC ... B01J 29/80; B01J 20/18; B01J 23/75; B01J 23/24; B01J 23/42; B01J 21/06; B01J 21/08
USPC ....................................................... 568/653
See application file for complete search history.

(56) References Cited

U.S. PATENT DOCUMENTS

| | | |
|---|---|---|
| 4,493,902 A | 1/1985 | Brown et al. |
| 4,802,971 A | 2/1989 | Herbst et al. |
| (Continued) | | |

OTHER PUBLICATIONS

Lin and Huber, Energy & Enviromental Science (2009), vol. 2, pp. 68-80.*

(Continued)

*Primary Examiner* — Kamal Saeed
*Assistant Examiner* — Janet L Coppins
(74) *Attorney, Agent, or Firm* — Foley & Lardner LLP

(57) ABSTRACT

A novel catalyst blend for processing of feedstocks into monoaromatics in a single stage, comprising at least one cracking catalyst, one heterogeneous transition metal catalyst, and optionally at least one hydrogenation catalyst. The process occurs in one-step or single stage with substantially no solvents or external additives, or when the feedstock contains less than 15% oxygen, the process includes additional water or steam to enable sufficient amounts of $H_2$ being produced in-situ.

21 Claims, 1 Drawing Sheet

(51) Int. Cl.
*B01J 21/00* (2006.01)
*B01J 29/80* (2006.01)
*B01J 23/656* (2006.01)
*B01J 35/00* (2006.01)
*C07C 1/20* (2006.01)
*C07C 37/52* (2006.01)
*C07C 41/01* (2006.01)
*C07C 27/00* (2006.01)
*B01J 37/04* (2006.01)
*B01J 29/06* (2006.01)
*C10G 3/00* (2006.01)
*C01B 3/16* (2006.01)
*B01J 29/08* (2006.01)
*B01J 23/755* (2006.01)
*B01J 35/08* (2006.01)
*B01J 29/40* (2006.01)
*B01J 21/08* (2006.01)
*B01J 21/06* (2006.01)
*B01J 23/24* (2006.01)
*B01J 23/42* (2006.01)
*B01J 23/16* (2006.01)
*B01J 37/02* (2006.01)
*B01J 29/16* (2006.01)
*B01J 29/48* (2006.01)
*B01J 29/87* (2006.01)

(52) U.S. Cl.
CPC .... *C07C 2523/42* (2013.01); *C07C 2523/656* (2013.01); *C07C 2523/755* (2013.01); *C07C 2529/40* (2013.01); *C07C 2529/80* (2013.01); *C10G 2300/1014* (2013.01); *C10G 2400/30* (2013.01); *Y02P 20/52* (2015.11); *Y02P 20/588* (2015.11)

(56) References Cited

U.S. PATENT DOCUMENTS

| | | | |
|---|---|---|---|
| 6,656,347 B2 | 12/2003 | Stockwell et al. | |
| 6,716,338 B2 | 4/2004 | Madon et al. | |
| 7,150,866 B2 | 12/2006 | Wieland et al. | |
| 8,404,908 B2 | 3/2013 | Chen | |
| 8,487,142 B2 | 7/2013 | Sarkar et al. | |
| 2005/0031920 A1 | 2/2005 | Igarashi et al. | |
| 2009/0227823 A1* | 9/2009 | Huber | C10G 1/002 585/324 |
| 2011/0201854 A1 | 8/2011 | Kocal et al. | |
| 2012/0193269 A1* | 8/2012 | Taha | C10G 11/05 208/95 |
| 2013/0030228 A1 | 1/2013 | Chen | |
| 2013/0060070 A1 | 3/2013 | Huber et al. | |

OTHER PUBLICATIONS

Written Opinion of the Int. Searching Authority dated May 26, 2015.

* cited by examiner

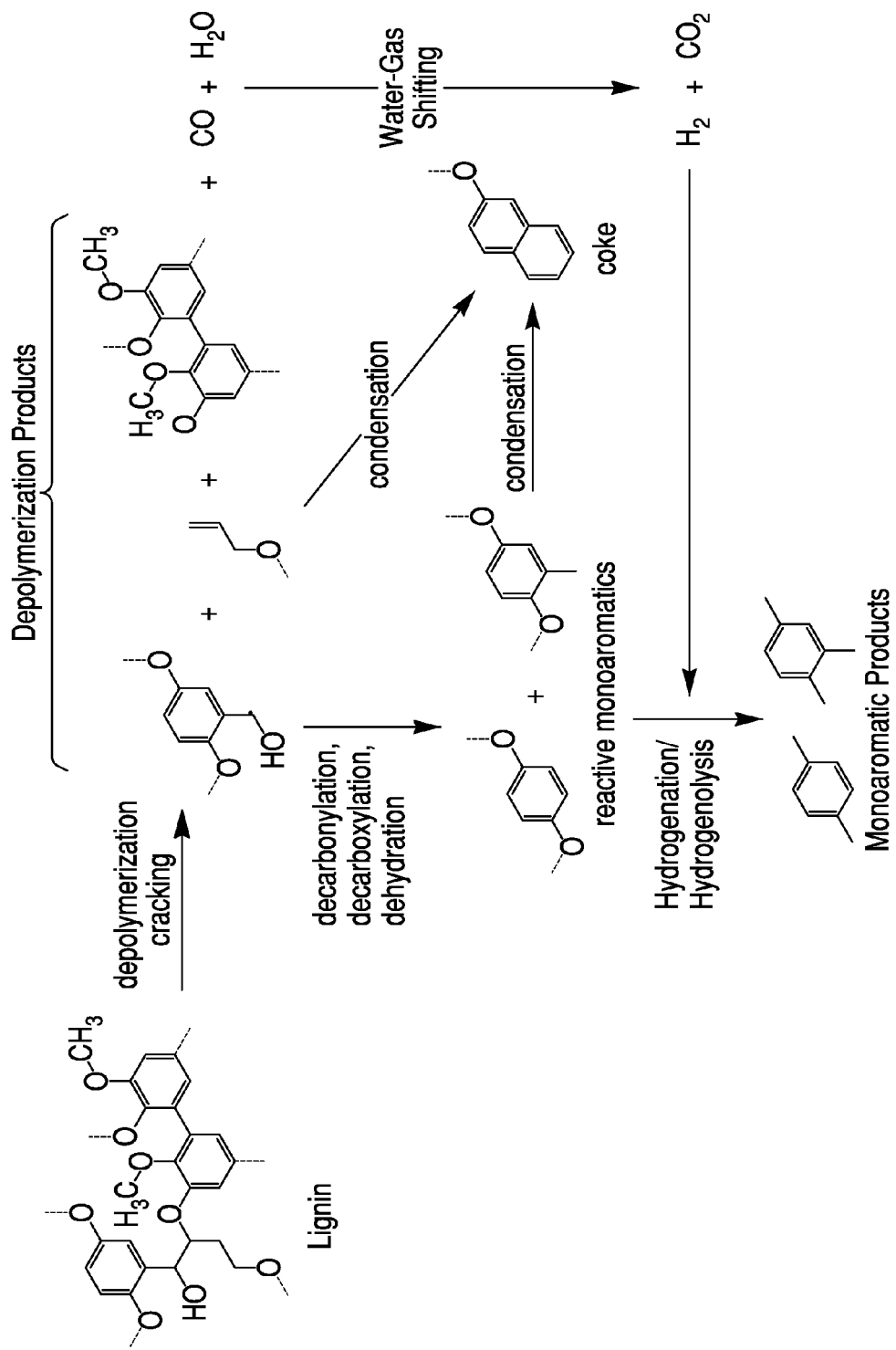

CATALYST FOR PYROLYSIS OF FEEDSTOCK

FIELD OF THE INVENTION

The present invention is directed to a single stage catalytic fast pyrolysis ("CFP") of feedstock using a novel catalyst blend.

BACKGROUND OF THE INVENTION

There is considerable current interest in the production of liquid fuels and chemical precursors from bio-derived waste materials, or polymer-containing feedstock.

Lignocellulosic biomass is of particular interest as a feedstock for production of renewable liquid biofuels and other commercially valuable compounds. It is a major structural component of woody and non-woody plants and consists of cellulose, hemicellulose and lignin. The aromatic carbohydrate polymers found in lignocellulosic biomass (primarily lignin) are of interest for production of high value platform chemicals, including monoaromatic compounds such as benzene, toluene, xylene, caprolactum, phenol, and their derivatives (e.g., guaiacol and catechol), which can be used for making a variety of chemicals and materials. Platform chemicals are important precursors for solvents, fuels, polymers, pharmaceutical, perfumes and foods.

Conversion of lignocellulosic biomass or a bio-derived feedstocks by pyrolysis involves many reaction steps leading to a liquid product that contains multiple components as well as significant water vapor, carbon oxides, and coke. The conversion process may be uncatalyzed, but catalysis improves the quality of the liquid product by removing oxygen in the liquid product, increasing the H:C ratio, and increasing the overall yield. Current methods for conversion of solid biomass to liquid components such as fuel involve multiple steps and long processing times, which greatly increases the cost of biomass processing. One process that has emerged as a viable technology to achieve such goals is fast pyrolysis. Fast pyrolysis converts many bio-derived materials to liquid hydrocarbons through a reductive conversion at elevated temperatures in a short amount of time.

It is envisioned that small conversion plants can be located nearby to large sources of biomass and convert the material to a liquid form which can be easily transported using existing infrastructure to refineries and chemical plants to be (co)processed in conventional hydrocarbon processing equipment. In order to realize this vision, the liquid products produced must possess properties which will allow for processing similar to fossil hydrocarbons and the value of the derived liquids and products must be sufficient to offset the added costs of the biomass processing step. For these reasons it is recognized that catalysts are needed in order to tune the properties and yields of the products. The catalyzed process is often referred to as catalytic fast pyrolysis (CFP).

CFP employs rapid heating of biomass in a non-oxidizing atmosphere to temperatures in the range of 400° C. to 600° C. in the presence of zeolite catalysts, and converts the biomass in a single step to gasoline-compatible aromatics. Although CFP requires shorter residence times and uses inexpensive catalysts, in general, the conversion of lignin and other biomass components to liquid hydrocarbons via CFP suffers from high coke yields and an acidic liquid product that has a high fraction of oxygen remaining. Furthermore, CFP produces large quantities of CO and $CO_2$ as well as steam. The cause of all of these observations can be traced back to the oxygen content of the feed and the type of reactions that occur over conventional depolymerization catalysts. The cracking of carbohydrates, unlike hydrocarbons, results in the formation of highly reactive oxygenates. These oxygenates tend to condense with other oxygen containing moieties or with olefins to form coke. Any remaining oxygenates contribute to the acidity of the final product and the presence of oxygen in the reactor results in formation of CO, $CO_2$, and steam. Thus, a catalyst for lignin CFP must be designed with these additional reactions taken into consideration. Typically, processing of biomass can also be done in a two-step process, wherein fast pyrolysis at 500° C.-700° C. is followed by catalyzed pyrolysis at about 400° C. The two-step process increases the yield of liquid, but is economically unfeasible. Further, it is desirable to use minimal or no external additives such as gases or liquids, other than the starting materials to reduce the operation and material cost in CPF processes.

Multi-step CFPs and/or CFPs that utilize additives are well known in the industry. For example, U.S. Patent Publication No. 2013/0030228 to Chen teaches a method to produce an aromatic hydrocarbon-containing effluent comprises the step of rapidly heating a biomass-based feedstock in the presence of a catalyst, hydrogen, and an organic solvent to form the aromatic hydrocarbon-containing effluent.

U.S. Patent Publication No. 2009/0227823 to Huber teaches compositions and methods for fluid hydrocarbon product via catalytic pyrolysis, which involves the use of a composition comprising a mixture of a solid hydrocarbonaceous material and a heterogeneous pyrolytic catalyst component.

U.S. Patent Publication No. 2013/0060070 to Huber teaches a method for producing one or more fluid hydrocarbon products from a solid hydrocarbonaceous material comprising: feeding solid hydrocarbonaceous material and hydrogen or a source of hydrogen to a reactor, then pyrolyzing the solid hydrocarbonaceous material, and catalytically reacting pyrolysis products and hydrogen to produce the one or more fluid hydrocarbon products.

U.S. Pat. No. 8,487,142 to Sarkar teaches a process for producing small molecular weight organic compounds from carbonaceous material, comprising a step of contacting the carbonaceous material with carbon monoxide (CO) and steam in the presence of a shift catalyst at a predetermined temperature and pressure.

U.S. Pat. No. 8,404,908 to Chen teaches a process includes reacting lignin with a hydrogenation catalyst under a hydrogen atmosphere to convert acidic oxygenate compounds to less acidic oxygenates or hydrocarbons. The oxygenate compounds are reacted in a dehydrogenation and a deoxygenation process to remove the oxygen, and to convert the cyclic hydrocarbons back to aromatic compounds.

The above-mentioned prior art teaches multi-steps or multi-stage processes, or the addition of external additives such as solvents and/or gases to initiate the depolymerization process of carbonaceous materials. Thus, there is a need for a single stage, one-pot process using a catalyst composition with minimal or no additives to produce liquid depolymerization products from polymers, such as production of monoaromatic compounds from lignin and lignocellulosic feedstock, with improved yields, reduced production of coke, and management of carbon monoxide. There is also a need for catalyst compositions that provide more economically viable processes by incorporating multiple catalytic functionalities in a single composition, thereby reducing the number of process steps required.

SUMMARY OF THE INVENTION

The invention is directed towards a novel catalyst blend for a single stage catalytic fast pyrolysis ("CFP") of feedstock, comprising: 1) at least one cracking catalyst; 2) a heterogeneous transition metal water-gas shift catalyst; and, optionally 3) as least one hydrogenation catalyst. The invention is also directed towards a single stage catalytic fast pyrolysis of feedstock using the novel catalyst blend, to produce monoaromatic products with substantially no solvents or other external additives. Alternatively, for feedstock that contains less than 15% of oxygen, the invention is also directed towards a single stage catalytic fast pyrolysis using the novel catalyst blend with additional water or steam to produce monoaromatics.

The novel catalytic blend produces exceptionally high amounts of monoaromatics that are useful intermediates for downstream commercial products, as compared to conventional catalysts known in the art.

BRIEF DESCRIPTION OF THE DRAWINGS

For a fuller understanding of the nature and advantage of the present invention, reference should be made to the following detailed description read in conjunction with the accompanying drawings.

FIG. 1 illustrates the steps of catalytic fast pyrolysis of aromatic polymers to monoaromatics using the novel catalyst blend that perfumes catalytic cracking, water-gas shifting and, optionally hydrogenation.

DETAILED DESCRIPTION

The invention is directed towards a novel catalyst blend for a single stage catalytic fast pyrolysis ("CFP") of feedstock, comprising: 1) at least one zeolite cracking catalyst; 2) a heterogeneous transition metal water-gas shift catalyst; and, optionally 3) as least one hydrogenation catalyst. The invention is also directed towards assessing oxygen content of the feedstock, such that at an oxygen content of greater than 15 wt %, the feedstock undergoes a single stage catalytic fast pyrolysis using the novel catalyst blend to produce monoaromatic products with substantially no solvents or other external additives. Alternatively, for the feedstock having an oxygen content of less than 15 wt %, the feedstock underwent single stage CFP with the novel catalyst blend and additional water or steam to ensure sufficient amounts of hydrogen gas is produced in-situ for hydrogenation.

The novel catalytic blend produces exceptionally high amounts of monoaromatics that are useful intermediates for downstream commercial products, as compared to conventional catalysts known in the art.

The terms "feedstock" and "biomass feedstock" refer to the plant-based raw material, which contains aromatic CHO polymers of high molecular weight and high boiling point. Included in this definition is "lignocellulosic biomass", which refers to plant matter composed of carbohydrate polymers (e.g., cellulose, hemicellulose) and the aromatic polymer lignin. The carbohydrate polymers are typically bound to lignin in lignocellulosic biomass. Lignocellulose is a suitable feedstock or substrate for the methods of the invention, wherein the high molecular weight aromatic CHO polymers are depolymerized and converted to more valuable monoaromatic products. Alternative suitable feedstocks include any material that contains plant-based materials but is not obtained directly from plants, e.g., manure, municipal waste (such as food waste or sewage), and biomass obtained from enzymatic processing of the cellulose in plant material.

The term "depolymerization products" refers to monomeric or oligomeric compounds produced by depolymerization of polymers within the feedstock. These products are of lower molecular weight than the polymer from which they are derived, and include compounds useful as platform chemicals, synthetic gas, and synthetic oil. Due to their reduced molecular weight, these products are liquid, whereas the polymer from which they are derived by depolymerization is a solid.

The phrase "reactive monoaromatics" and its equivalents refer to monoaromatic compounds derived from 1) depolymerization of the aromatic CHO polymer-containing feedstock, and 2) by decarbonylation, decarboxylation, and/or dehydration of depolymerization products produced by depolymerization.

The terms "monoaromatics", "monoaromatic compounds" and "monoaromatic products" are used interchangeably, and refer to as the end-product monomers derived from reactive monoaromatics in the present CFP process. These products are of benzyl compounds, phenolic compounds, and derivatives thereof such as 2-methoxy-phenol, 1,2-benzenediol, 4-ethyl-2-methoxy-phenol, 2-methoxy-6-methylphenol, 2-methoxy-4-(1-propenyl)-phenol, phenol, 2-methoxy-4-propyl-phenol, ethanone, 1-(4-hydroxy-3-methoxyphenyl)-phenol, 3-methyl-phenol, 2-methoxy-4-methylphenol. The monoaromatics are characterized by a boiling point of less than 220° C.

The term "microspheres" refers to small porous particles generally formed by spray drying. As is understood by skilled artisans, microspheres are not necessarily perfectly spherical in shape. Microspheres have a diameter in the micrometer or micron range (about 1-999 µm).

The term "matrix component" refers to the structural support component of the microspheres, which is generally a relatively inert material (i.e., not the catalytically active component). For example, the matrix component can be selected from the group consisting of kaolinite, halloysite, montmorillonite, bentonite, attapulgite, kaolin, amorphous kaolin, metakaolin, mullite, spinel, hydrous kaolin, clay, gibbsite (alumina trihydrate), boehmite, titania, alumina, silica, silica-alumina, silica-magnesia, magnesia and sepiolite.

The term "in-situ crystallized" refers to the process in which a zeolite is grown or intergrown directly on/in a microsphere and is intimately associated with the matrix component for example, as described in U.S. Pat. Nos. 4,493,902 and 6,656,347. One suitable method for preparation of porous microspheres carrying one or more in-situ crystallized zeolites is described in U.S. Pat. No. 6,716,338.

The phrase "substantially no solvents or other external additives" is equivalent to "substantially free of solvents or other external additives", refers to less than 5%, preferably less than 1%, and more preferably less than 0.5% of the total reaction mixture of the feedstock and the novel catalyst blend, such that the additives contribute to no significant effects on CFP and the subsequent production of monoaromatics.

Cracking Catalyst

Cracking catalysts useful for the present invention are catalysts that facilitate breaking (i.e., depolymerization or "cracking") of the covalent oxygen-containing bonds of the aromatic CHO polymer to produce smaller aromatic CHO polymers (including dimers and trimers) and oligomers. Depolymerization or cracking catalysts suitable for use in the invention include, but are not limited to, zeolitic catalysts as well as non-zeolitic catalysts (e.g., molecular sieves, solid acid catalysts, WOx/ZrOz, alumina, phosphate, etc.).

For catalytic fast pyrolysis processes ("CFP"), particularly advantageous cracking catalysts may include those containing internal porosity selected according to pore size (e.g. mesoporous and pore sizes typically associated with zeolites), e.g., average pore sizes of less than about 100 Angstroms, less than about 50 Angstroms, less than about 20 Angstroms, less than about 10 Angstroms, less than about 5 Angstroms, or smaller. In some embodiments, catalysts with average pore sizes of from about 5 Angstroms to about 100 Angstroms may be used. In some embodiments, catalysts with average pore sizes of between about 5.5 Angstroms and about 6.5 Angstroms, or between about 5.9 Angstroms and about 6.3 Angstroms may be used. In some cases, catalysts with average pore sizes of between about 7 Angstroms and about 8 Angstroms, or between about 7.2 Angstroms and about 7.8 Angstroms may be used.

In some embodiments of CFP, the zeolite catalyst may be selected from naturally occurring zeolites, synthetic zeolites and combinations thereof. The catalyst may be a ZSM-5 zeolite catalyst. The catalyst may comprise acidic sites. Other zeolite catalysts that may be used may include ferrierite, zeolite beta, Y zeolite, mordenite, MCM-22, ZSM-23, ZSM-57, SUZ-4, EU-1, ZSM-11, (S)AlP0-31, SSZ-23, SAPO, ALPA, MeALPO and the like.

In certain embodiments, a Mordenite Framework Inverted (MFI) zeolite catalyst comprising gallium can be used. For example, a galloaluminosilicate MFI (GaAlMFI) zeolite catalyst can be used. One of ordinary skill in the art would be familiar with GaAlMFI zeolites, which can be thought of as aluminosilicate MFI zeolites in which some of the Al atoms have been replaced with Ga atoms. In some instances, the zeolite catalyst can be in the hydrogen form (e.g., H—GaAlMFI). The galloaluminosilicate MFI catalyst can be a ZSM-5 zeolite catalyst in which some of the aluminum atoms have been replaced with gallium atoms, in some embodiments.

A screening method may be used to select catalysts with appropriate pore sizes for the conversion of specific pyrolysis product molecules. The screening method may comprise determining the size of pyrolysis product molecules desired to be catalytically reacted (e.g., the molecule kinetic diameters of the pyrolysis product molecules). One of ordinary skill in the art can calculate, for example, the kinetic diameter of a given molecule. The type of catalyst may then be chosen such that the pores of the catalyst (e.g., Norman adjusted minimum radii) are sufficiently large to allow the pyrolysis product molecules to diffuse into and/or react with the catalyst. In some embodiments, the catalysts are chosen such that their pore sizes are sufficiently small to prevent entry and/or reaction of pyrolysis products whose reaction would be undesirable.

It may be desirable, in some embodiments, to employ one or more catalysts to establish a bimodal distribution of pore sizes. In some cases, a single catalyst with a bimodal distribution of pore sizes may be used (e.g., a single catalyst that contains predominantly 5.9-6.3 Angstrom pores and 7-8 Angstrom pores). In other cases, a mixture of two or more catalysts may be employed to establish the bimodal distribution (e.g., a mixture of two catalysts, each catalyst type including a distinct range of average pore sizes).

The zeolite cracking catalyst of the present invention preferably comprises at least one of a large pore zeolite (consisting of 12-membered rings) and a small or intermediate pore zeolite (consisting of 8-10 membered rings). Examples include high matrix Y zeolite and ZSM-5. Y zeolite has large pores formed by 12-membered rings (about 7.4 Å pore diameter) and facilitates depolymerizing/cracking of the high molecular weight lignin feedstock. ZSM-5 is a pentasil zeolite with small to intermediate linear pores formed by 5-membered rings (approximately 5.4-5.6 Å diameter) that is a cracking or depolymerization catalyst, but can also provide selectivity for production of monoaromatic compounds from olefins produced as intermediates during pyrolysis.

Other large pore zeolite catalysts are equally suitable for use in the invention for depolymerization, for example 12 membered ring zeolites including framework types FAU, CHA, MOR and the like. Y zeolite is included in this group. Other small/intermediate pore zeolite catalysts consisting of 8-10 membered rings include framework types ACO, AEI, AEN, AFN, AFT, AFX, ANA, APC, APD, ATT, CDO, DDR, DFT, EAB, EDI, EPI, ERI, GIS, GOO, IHW, ITE, ITW, LEV, KFI, MER, MON, NSI, OWE, PAU, PHI, RHO, TH, SAT, SAV, SIV, THO, TSC, UEI, UFI, VNI, YUG, ZON, MFI, LTA, BEA and the like, and these are equally suitable for use in the invention for depolymerization and monoaromatic selectivity. Specific examples include, for example, ZSM-11, MFI zeolite and MCM. If a mixture of at least one large pore zeolite and at least one small zeolite are incorporated together to form the zeolite catalyst, the zeolite catalyst preferably has a ratio of large zeolites to small zeolites from 10:1 to 1:10, preferably from 5:1 to 1:5, and more preferably from 3:1 to 1:3, based on the total weight of the zeolite catalyst.

The cracking catalyst is supported on a solid support. The solid support may be in the form of porous microspheres to provide increased surface area for the catalytic reactions. The pores of the microspheres are typically selected such that they are large enough to allow access by large polymers, such as aromatic CHO polymers, in the feedstock. The depolymerization catalyst may be either incorporated into microspheres, or formed in-situ within microspheres. In certain specific embodiments, the depolymerization catalyst (e.g., a Y zeolite) is crystallized in-situ within the pores of the microspheres. In certain specific embodiments, the porous microspheres are about 70-90 μm in diameter, or about 80 μm in diameter. In further specific embodiments, the porous microspheres have a majority of pores in the range of about 90-110 nm in diameter, or about 100 nm in diameter. Suitable microspheres with in-situ crystallized zeolite may be produced as described in U.S. Pat. No. 4,493,902, which is incorporated herein by reference.

Water-Gas Shift Catalyst

The catalyst blend further includes a heterogeneous transition metal water-gas shifting catalyst. The water-gas shift catalyst generates in-situ partial pressure of hydrogen from water vapor and carbon monoxide produced during pyrolysis of lignin or feedstock. The in-situ partial pressure hydrogen reacts with the reactive monoaromatics, with or without the presence of a hydrogenation catalyst to produce end-product monoaromatics.

The heterogeneous transition metal catalyst is comprised of at least one metal catalyst on a support, which is optionally promoted by a metal acid promoter. The metal catalyst is selected from platinum, palladium, ruthenium, rhenium rhodium, osmium, iridium, nickel, cobalt, molybdenum, copper, tin, iron, zinc, gold, silver, or mixtures thereof. The support is selected from the group consisting of zirconium, silica, $Al_2O_3$ (Alumina), $TiO_2$, and mixtures thereof. The support is optionally acid promoted by an acid promoter selected from tungsten, niobium, molybdenum, cerium, manganese, vanadium, rhenium, and tantalum.

Preferably, the metal catalyst is selected from the group consisting of platinum, palladium, ruthenium, rhenium, rhodium, and mixtures thereof. The metal catalyst may contribute to hydrogenation, hydrogenolysis, decarbonylation, and decarboxylation in the CFP process. The amount of metal catalyst or metal catalyst mixture in the water-gas shift catalyst is about 0.01% to about 20% by weight; preferably about 0.5% to about 10%; more preferably about 0.5% to about 5%; most preferably 0.5% to about 2% by weight, or about 0.5% to about 1% by weight is also useful. More preferably, the heterogeneous water-gas shift catalyst contains at least one metal or metal oxide on a promoted support, at least two metals or metal oxides on a support that is optionally promoted.

At least one metal catalyst is supported on zirconium, silica, $Al_2O_3$, $TiO_2$, or mixtures thereof. The support is optionally promoted by a metal acid promoter, which may contribute to dehydration, hydrolysis, or both in the CFP process. An acid promoter can increase the acidity of the support and create additional acid sites. In one embodiment the acid promoter is selected from tungsten, niobium, molybdenum, cerium, manganese, vanadium, rhenium, and tantalum. The acid promoter may be a combination of more than one metal. In another embodiment the acid promoter is selected from tungsten, niobium, and molybdenum. In another embodiment the acid promoter is molybdenum. In one embodiment the amount of acid promoter may be from about 0.01% to about 99% by weight of the support. In another embodiment the amount of acid promoter may be from 0.1% to about 50%; about 0.5% to about 25%; about 1% to about 15%; or about 5% to about 10% by weight of the support.

The acid promoter is typically added to the support by the incipient wetness method or impregnation method, which is then followed by the addition of the active metal(s). The support here is typically referred to the shaped support with crush strength above 1.5 lb/mm. The acid promoter is dissolved in solvent, typically, in water, and added to the support by incipient wetness or impregnation method, or any other method to effectively disperse promoter into the support. The mixture is then dried and followed by calcinations at high temperature. The process may be repeated to add additional acid promoter to the support. In another embodiment, the acid promoter is added by physically mixing the promoters with the support before extrusion and calcinations. In another embodiment, the acid promoter is added by precipitation with base into the support slurry followed by filtration, dry, extrusion, calcination. The acid promoter precursors are water soluble salts, metal oxides, metal hydroxides. In one embodiment, the acid promoter precursors are ammonia niobate oxalate, ammonia metatungstate hydrate, ammonium molybdate tetrahydrates, molybdic acid sodium salt dehydrate, niobic acid and tungstic acid.

Changing the acid promoter, the amount, and the calcination temperature, and/or the combinations of acid promoters will change the number of acid sites and the acid strength of the catalyst support.

The water-gas shift catalyst may be formed by adding the metal catalyst precursor to the optionally promoted support by the conventional incipient wetness method, or by the impregnation method, or any other method to disperse the method onto the support effectively. The incipient wetness method involves dropping the catalyst precursor solution onto the earner until completely wets the carrier followed by drying and calcination. In other words, the volume of the precursor solution consumed is equal to the total pore volume of carrier. In order to achieve the desired the loading, the above procedure may be repeated several times. The impregnation method involves placing the support in a solution containing excess dissolved catalyst precursor with heat and stirring. The support is removed from the solution and is then dried and calcined. In one embodiment, the metal catalyst precursor is dissolved in a solvent (one example is water) prior to adding to the support. The wet materials are dried followed by heating at a controlled rate to a temperature of about 450° C. for calcining the material.

Preferably, the water-gas shift catalyst is comprised of at least two metal oxides selected from platinum, rhenium, iron, cobalt, and mixtures thereof; a support that is selected from the group consisting of $Al_2O_3$ and silica, wherein the support is promoted by cerium, molybdenum, and tungsten. More preferably, the transition metal water-gas shift catalyst is comprised of a mixture of platinum and rhenium, and an $Al_2O_3$ support that is promoted by molybdenum.

Hydrogenation Catalyst

The hydrogenation catalyst hydrogenates reactive monoaromatics derived from lignin before they are able to condense and re-polymerize into coke. In one or more embodiments, the hydrogenation catalyst may be a base metal or base metal oxide supported by $Al_2O_3$, silica, or other inert matrix. In further specific embodiments the base metal or base metal oxide is selected from the group consisting of nickel (Ni), copper (Cu), zinc (Zn), and combinations thereof, wherein the base metal is of 30-90 wt %, preferably 50-85 wt %, and more preferably 60-80 wt % of the hydrogenation catalyst. Preferably, the hydrogenation catalyst is an oxide of Ni.

It must be noted that the present inventive catalyst blend optionally includes the hydrogenation catalyst. The hydrogenation catalyst is optional because hydrogenation can still occur with reactive monoaromatics in-situ, with the presence of hydrogen gas which is generated by a water-gas shift catalyst.

In any of the foregoing embodiments, the catalyst blend comprises about 20-90 wt %, preferably about 40-85 wt %, and most preferably about 50-80 wt % of the cracking catalyst(s); about 3-80 wt %, preferably about 5-40 wt %, and most preferably about 7-20 wt % of the heterogeneous transition metal water-gas shift catalyst; and optionally about 3-20 wt %, preferably 5-15 wt %, and most preferably 7-10 wt % of the hydrogenation catalyst(s), based on the total weight of the catalyst blend. It will also be understood that because zeolites are subject to decomposition over time in the process, thus when zeolites are employed as the cracking catalyst, it may be desirable to increase the amount of zeolite catalyst in the inventive catalyst blend to compensate and provide a longer useful catalytic life. For example, in certain situations, the zeolite cracking catalyst may be present in the catalyst composition in an amount from about 40-90 wt %. Overall, the catalyst blend comprise a total of about 25-90 wt %, preferably 35-85 wt %, and more preferably 40-80 wt % of zeolite within the zeolite cracking catalyst; about 7-10 wt %, preferably 7.5 wt % of a water-gas shift catalyst that is comprised of Mo-promoted Pt and Re oxides (e.g., 5.6 wt % Pt oxide and 3 wt % Re oxide); and optionally about 7-10 wt %, preferably 7.5 wt % of a hydrogenation catalyst comprising NiO, based on the total weight of the catalyst blend. Specifically, the water-gas shift catalyst contains 6.61% of $PtO_2$, 3.88% of $Re_2O_7$, and 0.715% of $MoO_3$. In another embodiment, overall concentrations of the components are 0.5% $PtO_2$, 0.3% $Re_2O_7$, 0.05% MoO$_3$ and 5.5% NiO in the final catalyst blend. The individual catalysts are mixed together in the desired proportions as particulate or powder components.

Method of Production

The cracking or depolymerization catalyst(s), the water-gas shift catalyst, and optionally the hydrogenation catalyst may be incorporated into or on porous microspheres, which are generally comprised of an inert matrix material such as calcined kaolin clay. Other inert components that may be used in the catalyst compositions include additional clays, binders, and the like. In one or more embodiments, the at least one zeolite of the catalyst blend may be in the form of a zeolite crystallized in-situ in the pores of microspheres comprised of an inert matrix such as calcined kaolin clay.

Large pore zeolite cracking catalysts, having pore openings of greater than about 7 Å in effective diameter are particularly useful for in-situ crystallization into the pores of the microspheres because they are selective for depolymerization of the large polymers. Examples of such large pore zeolites include zeolite X; REX; Y zeolite; Ultrastable Y (USY); Rare Earth exchanged Y (REY); Rare Earth exchanged USY (REUSY); Dealuminated Y (DeAl Y); Ultrahydrophobic Y (UHPY); and/or dealuminated silicon-enriched zeolites, e.g., LZ-210. The large pore zeolite may be crystallized in-situ as described above, or it may be prepared by spray drying into a particulate formulation that is mixed in the catalyst blend. Addition of at least a second zeolite having pores with a smaller effective diameter and selectivity for production of the smaller monoaromatics from olefins produced in the depolymerization process, is also useful in the catalyst blend. One example of a suitable small pore zeolite is ZSM-5, which has an eight ring linear pore configuration. Other suitable examples of such small/intermediate pore zeolites include ZSM-11, MFI zeolite and MCM. The small pore zeolite may be crystallized in-situ in calcined clay microspheres, but may also be spray dried into a particulate formulation that is mixed in the multifunctional catalyst compositions.

Alternatively, zeolite incorporation onto microspheres involves: crystallizing the zeolite and then combine with clay, binder, alumina, etc. in slurry and spray drying to form the active microsphere. Post treatments like exchanges and calcination would be applied similar to the in-situ method.

An example of a microsphere particles useful in any of the multifunctional catalyst compositions described herein are described in U.S. Pat. No. 6,716,338, which is incorporated herein by reference. These microspheres initially comprise hydrous kaolin clay and/or metakaolin, optionally a dispersible boehmite, optionally spinel and/or mullite, and a sodium silicate or silica sol binder as the matrix component, but are subsequently calcined to convert hydrous kaolin to metakaolin and boehmite to transition alumina. Any of the zeolite catalysts useful in the invention may be prepared in this manner. If desired, the zeolitic cracking catalysts can then be crystallized in-situ in the desired amount in the pores of the microspheres by reaction with an alkaline sodium silicate solution and ion exchange.

Method of Use (CFP)

Embodiments of the invention also provide methods for producing liquid depolymerization products from oxygen-containing polymer feedstock (for example, monoaromatics from aromatic CHO polymer-containing feedstock) using any of the integrated multi-functional catalyst compositions described above. In certain embodiments, the feedstock has an oxygen content of at least 15% by weight, for example about 15-50% by weight or about 15-30% by weight. Aromatic CHO polymer containing feedstock may include lignins. The methods of the invention are useful for isolation of monoaromatics from aromatic CHO polymer containing feedstock including, for example, benzyl compounds and phenolic compounds, and are capable of converting at least 15 wt % of the feedstock feed to monoaromatics.

In one or more embodiments, the methods for producing depolymerization products or monoaromatics from an oxygen-containing polymer feedstock is comprised of: a) assessing oxygen content of a feedstock; b) for feedstock having an oxygen content of at least 15%, reacting the feedstock containing oxygen-contained polymers with a catalyst blend comprising at least one cracking or depolymerization catalyst, a heterogeneous transition metal water-gas shift catalyst, and optionally at least one hydrogenation catalyst, wherein the reaction mixtures include substantially no solvents or other external additives; alternatively, for feedstock that contains an oxygen content of less than 15%, additional water or steam is added to the reaction mixture, such that the novel catalyst blend cracks the feedstock, converting carbon monoxide (CO) and water (H$_2$O) produced during depolymerization to hydrogen (H$_2$), and hydrogenating reactive monomers and intermediates (e.g., reactive monoaromatic compounds) to produce the liquid depolymerization products (e.g., monoaromatic compounds); and c) recovering the compounds of the liquid depolymerization products.

The method to produce monoaromatics of the present invention further includes a means to assess the oxygen content of the feedstock, and a means to dispense appropriate amounts of water or steam into the feedstock/catalyst blend reaction mixture, to ensure sufficient amounts of hydrogen is produced in-situ for hydrogenation. The water or steam, if required, is preferably dispensed into the reactor with a lift gas. Specifically, the steam content was controlled by the addition of water at 0.1 ml/min for the duration of each cracking experiment, to enable sufficient amounts of hydrogen gas being produced in-situ for the hydrogenation reaction.

In certain embodiments, the operating temperature for the depolymerization, water-gas shift and hydrogenation reactions is about 350° C. to 600° C., about 400 to 500° C., or about 350 to 450° C. Preferably, the operating temperature for the depolymerization, water-gas shift and hydrogenation reactions is about 400 to 500° C. Although the process can be performed at elevated pressure, a particular advantage of using the catalyst blend is that the process proceeds efficiently at low pressure, e.g., atmospheric pressure or about 1-2 atm. Preferably, the CFP process of the present invention is complete within 15 minutes, more preferably within 10 minutes, and most preferably within 5 minutes.

The theoretical chemistry of the process for producing monoaromatic compounds from aromatic CHO polymer-containing feedstock is again illustrated in FIG. 1. In a first step, the aromatic CHO polymer depolymerization catalyst component of the catalyst blend "cracks" the aromatic CHO polymer(s) (i.e. lignin) contained in the feedstock, to produce a mixture of monoaromatic compounds, oligomers or shorter polymeric compounds such as dimers and trimers, olefins, CO and water. When a second aromatic CHO polymer depolymerization catalyst that is selective for production of monoaromatic compounds from olefins is present, such as ZSM-5 zeolite, olefins are converted to monoaromatics rather than condensing to coke. Decarbonylation, decarboxylation and dehydration of the monoaromatic compounds initially produced by cracking results in reactive monoaromatics that are capable of reforming dimeric and trimeric aromatic compounds.

The water-gas-shift catalyst(s) convert carbon monoxide and water produced during the depolymerization step to hydrogen according to the following reaction:

$$CO + H_2O \longleftrightarrow CO_2 + H_2$$

Hydrogenation of these reactive monoaromatics using hydrogen produced in the concurrent WGS reaction stabilizes them, prevents re-polymerization, and produces the final monoaromatic product which can be recovered using techniques known in the art. The reaction steps as shown in FIG. 1 occur continuously (i.e. currently) and in the same reactor without any additional solvents or gases to initiate the depolymerization. FIG. 1 also illustrates a side reaction of the cracking process in which condensation of products of the cracking process re-condense to produce coke. Coke is an undesirable reaction product that causes increases in the heat that is generated by burning off the coke during the highly exothermic regeneration of the catalyst in commercial catalytic cracking processes. Catalysts that result in a high level of conversion to coke have limited utility in commercial processes, even if they are highly catalytically active.

The first step of the process for producing liquid depolymerization products from oxygen-containing polymers in polymer-containing feedstock typically involves mixing the feedstock and the catalyst blend at a desired catalyst:feed ratio. The proportion of catalyst:feed is generally selected based on the amount of oxygen-containing polymer present in the feed. In certain embodiments, the ratio of the catalyst blend to oxygen-containing polymer is about 2-10:1 by weight, about 4-9:1 by weight, about 9:1 by weight or about 5:1 by weight. The mixture is then placed in a reactor at about 400° C. for pyrolysis and held at that temperature during the catalytic reaction. Liquid products are condensed and collected. The products that have a boiling point of less than 220° C. are the desired monoaromatic compounds.

In any of the foregoing methods for producing monoaromatic compounds from aromatic CHO polymer-containing feedstock, the feedstock may be sourced from any aromatic CHO polymer-containing material, such as virgin biomass (trees, bushes and grass), agricultural residues (e.g., corn stalks or ears, straw, sugarcane bagasse etc.), pellets of processed biomass, wood chips and residues (e.g., waste from sawmills and pulping processes), and energy crops produced as raw material for production of biofuel (e.g., switch grass or elephant grass). Preferably, the monoaromatic compounds are produced from lignin contained in the feedstock.

Also in any of the foregoing methods for producing liquid depolymerization products from oxygen-containing polymers in feedstock, the feedstock may also comprise polymers such as polyphenyl ethers (PPE), polyphenylene oxides (PPO), polyoxymethylene (POM), polyethylene oxide (PEO), polypropylene oxide (PPO), polytetrahydrofuran (PTHF), and/or polycarbonates and polyesters (including aliphatic, semi-aromatic and aromatic variants).

In certain embodiments of the foregoing methods, the process for the single stage conversion of feedstock is implemented in a circulating fluid-bed catalytic cracking (FCC) system similar to the FCC process used for processing petroleum; however, it will be recognized that, unlike petroleum processing, the feedstock in the present process the feedstock is a solid rather than a liquid. The oxygen-containing polymers present in feedstock, such as lignin, have some common characteristics to petroleum. For example, they are high molecular weight polymers with high aromatic content that are difficult to process chemically. The catalyst blend of the present invention makes it possible to adapt polymer depolymerization and lignin bioprocessing to commercially used FCC systems for processing petroleum.

In the CFP process of the present invention, the hot integrated catalyst blend is added as a powder or particulate material, suspended in the oxygen-containing polymer feedstock, and propelled upward in the riser section of the FCC unit into a reaction zone where the feedstock is cracked at an elevated temperature. A lift gas such as nitrogen is admixed with the catalyst to provide a fluidized suspension. The reaction products and spent catalyst are then discharged from the riser into a separator where the reaction products are conveyed to a recovery zone and the catalyst is sent to a catalyst regenerator unit. The fluidized catalyst is continuously circulated between the riser and the regenerator to supply heat for the cracking reaction, and to maintain the feed at the desired reaction temperature. Preferably in the CFP process of the present invention, as the fluidized catalyst blend and feed are directed upward in the reactor, the oxygen-containing polymers in the feed are depolymerized, and concurrently reactive liquid depolymerization products (reactive monoaromatics) are produced and hydrogenated to the final stable monoaromatic product. Also concurrently, CO produced during depolymerization is converted to $CO_2$ and $H_2$ in the presence of water by the water-gas shift catalyst and the in-situ $H_2$ is used in the hydrogenation.

As a result of pyrolysis, coke deposits on the catalyst, while the lighter, more valuable products of the catalytic reactions (including monomers, dimers, trimers and oligomers) exit the riser and enter a solid-gas separation system at the top of the reactor vessel where they are fractionated to isolate and recover the stable monoaromatic compounds. The coked catalyst is directed to the catalyst regeneration zone where the coke is burned off, typically at temperatures of 600° C. to 850° C., and then the catalyst is recycled back into the riser section of the FCC unit for continuous production of monoaromatics.

The CFP process of the present invention converts of at least 15 wt %, preferably at least 40 wt %, and more preferably at least 60 wt % of the feedstock to monoaromatic products.

The catalyst blend of the present invention provides a higher production of monomers and decreased amounts of dimers, trimers, and oligomers, as compared with the use of zeolites alone. There is also a decrease in coke production compared to zeolite alone, which results in improved regeneration and utility of the catalyst. A further advantage of the catalyst blend of the present invention relates to the ability to perform all of the steps of the reaction process concurrently, single stage is one reactor, as opposed to sequentially, thus providing a continuous process adaptable to commercial production processes such as FCC. Such a concurrent process not only eliminates sequential process steps, but the in-situ production of hydrogen directly from the feedstock eliminates the need for a separated external hydrogen input for maintaining an acceptable H:C ratio in the final product and improves the overall hydrogen management of such processes. The high efficiency of the process was unexpected in view of the single reaction temperature and pressure used for all catalytic reactions (e.g., about 350° C. to 600° C., about 400 to 500° C., about 350 to 450° C., or about 400° C., and 1-2 atm.). This temperature/pressure region is not generally well suited for hydrogenation when processing conventional feedstocks. However, the unique combination of catalytic functionalities and oxygen-containing feedstocks (including aromatic CHO polymer feedstocks), which produce reactive monomer intermediates during processing optimizes the overall thermodynamics and kinetics of the reactions. Thus, the three reactions (deploymerization, water-gas shift, and hydrogenation) are capable of being efficiently catalyzed under the lower temperatures and atmospheric pressure conditions of fixed bed and fluid bed reactors, even though these reaction conditions are not optimal for all of the catalysts in the composition.

EXAMPLES

Preparation of a Control Microsphere ("Control"): Negative (non-catalytic) control microspheres, consisting only of a calcined kaolin clay matrix component (i.e., no catalyst), were prepared from a spray dried kaolin slurry as described in U.S. Pat. No. 4,493,902, which is incorporated herein by reference.

Preparation of a Base Catalyst Microsphere ("Base"): A base catalyst composition comprising only Y zeolite and ZSM-5 zeolite catalysts was prepared by mixing 15% by weight of non-catalytic control microspheres (above), 35% by weight of STAMINA™ FCC catalyst (Y zeolite crystallized in-situ in a kaolin clay microsphere matrix, BASF), and 50% by weight ZSM-5 produced by spray drying a slurry containing the zeolite, kaolin, and a low surface area alumina as described in U.S. Pat. No. 7,375,048, which is incorporated herein by reference. The STAMINA™ FCC catalyst comprises about 40% by weight of the zeolite, and the ZSM-5 composition comprises at least about 30 wt % of ZSM-5. Accordingly, the Y zeolite component of the catalyst composition represented about 14% by weight and the ZSM-5 component of the catalyst composition represented at least about 15% by weight, with a total zeolite component of about 29% by weight of the base catalyst. Both FCC components were hydrothermally aged, by heating to 815° C. in the presence of steam for 4 hours, prior to blending and testing.

Preparation of an Experimental Catalyst I ("EC I"): The non-catalytic control microsphere component of the base catalyst composition was replaced with 7.5% by weight of a water-gas shift catalyst (Pt and Re oxides, 5.6 wt % $PtO_{2/3}$ wt % $ReO_2O_7$, on Mo-promoted $Al_2O_3$) and 7.5 wt % of a hydrogenation catalyst. The water-gas shift catalyst was prepared as follows: the catalyst support was impregnated with an aqueous solution of disodium molybdate (molybdic acid sodium salt dehydrate) followed calcination at 300° C. for 3 hours. The impregnated support was then impregnated with an aqueous solution of chloroplatinic acid and calcined again at 300° C. for 3 hours. Finally the sample was impregnated with an aqueous solution of ammonium perrhenate and then dried at 120° C. overnight followed by calcination at 5° C./min to 500° C. for 2 hours. The hydrogenation catalyst was a commercial hydrogenation catalyst (Ni 3298) containing 60 percent by weight nickel on alumina. The water-gas shift and hydrogenation catalysts were used without any further deactivation. The water-gas shift catalyst and hydrogenation catalysts were mixed into the composition as powders.

Preparation of an Experimental Catalyst II ("EC II"): The non-catalytic control microsphere component of the base catalyst composition was replaced with 7.5% by weight of a high temperature water-gas shift catalyst (Pt and Re oxides, 5.6 wt % $PtO_{2/3}$ wt % $ReO_2O_7$, on Mo-promoted $Al_2O_3$). The water-gas shift was used without any further deactivation. The water-gas shift catalyst was mixed into the composition as powders.

Depolymerization of Lignin and Production of Monoaromatics: Lignin feedstock was mixed, respectively with the base catalyst composition and the experimental catalyst I and the experimental catalyst II at a catalyst/feed ratio from 5:1 to 9:1 and placed in a fixed fluid bed reactor and heated to a reaction temperature of 400° C. The negative control microspheres were mixed with the lignin feedstock for the negative control reaction, with a catalyst/feed ratio of 0:1. The reactions were allowed to proceed for 15 min. after the reaction temperature was reached. Products were collected and analyzed following the termination of reaction. The system was continuously purged with nitrogen. Non-condensable gasses were analyzed by inline GC-MS. Liquid products were condensed in a water bath and collected for analysis and classification by HT-Sim Dis and DHA in a manner similar to analysis of hydrocarbon products obtained from gasoil cracking. These procedures provide quantitative analysis of products into categories based on boiling point and qualitative identification of some product components. Catalyst samples were retained for coke/char analysis.

Results

Water-Gas-Shift Reaction: A decrease in CO in the product gas was observed for the experimental catalyst I compared to both the non-catalytic control and the base catalyst. The decrease in CO was accompanied by an increase in hydrogen and carbon dioxide in the product gas as compared to the negative control and the base catalyst. These results indicate that the WGS reaction proceeded effectively under the reaction conditions of the fixed bed reactor.

TABLE 1

| | Gas Yields in wt % | | |
|---|---|---|---|
| | CO Yields (Carbon Monoxide) | $CO_2$ Yields (Carbon Dioxide) | $H_2$ Yields (Hydrogen) |
| Control | 0.15 | 2.37 | 0 |
| Base | 0.11 | 0.86 | 0 |
| EC I | 0.06 | 5.86 | 0.19 |

TABLE 2

| | Liquid Yields in wt % | | | |
|---|---|---|---|---|
| | Total Liquid Yield (wt %) | <220° C. | 220° C.- 340° | >340° C. |
| Control | 43.19 | 19.85 | 17.05 | 6.29 |
| Base | 55.32 | 37.2 | 16.07 | 2.04 |
| EC I | 50.02 | 39.4 | 9.57 | 1.05 |

The base catalyst (zeolite only) produced an increase in total liquid yields compared to the negative control. Although total liquid yield for the experimental catalyst I was slightly less than the base catalyst, the production of the desired monomers (<220° C.) was higher and the production of dimers/trimers (220° C.-340° C.) and oligomers (>340° C.) was lower.

A decrease in coke was observed with both the base catalyst (43.11 wt %) and the experimental catalyst (37.43 wt %) compared to the negative control (52.95 wt %), but the decrease in coke for the experimental catalyst was greater. These results suggest that monoaromatics produced by depolymerization using the experimental catalyst are concurrently stabilized by in-situ hydrogen generation from the water-gas shift reaction and hydrogenation by the hydrogenation catalyst.

TABLE 3

Coke and Monomer Yields in wt %

|  | Coke | <220° C. |
|---|---|---|
| Control | 52.95 | 19.85 |
| Base | 43.11 | 37.2 |
| EC I | 37.43 | 39.4 |

The samples were further tested and measured to obtain gas yield from organic liquid. Again, experimental catalyst I yielded lower amounts of coke and almost twice as much valued aromatic product (39.4 vs. 19.85).

TABLE 4

|  | Carbon | Hydrogen | Oxygen |
|---|---|---|---|
| Control | 68.08 | 10.86 | 21.07 |
| Base | 75.54 | 12.57 | 11.89 |
| EC I | 72.95 | 12.17 | 14.88 |
| EC II | 75.89 | 14.62 | 9.49 |

Table 4 shows the carbon, hydrogen, and oxygen content of the liquid produced from each reaction sample. From this data, it is clear that the experimental catalysts I and II offer significant advantages in oxygen removal, with experimental catalyst II showing more than 50% oxygen removal as compared to the uncatalyzed reaction.

TABLE 5

|  | Aromatic Yields* | Phenols Yields* | Undesired Yields* | |
|---|---|---|---|---|
|  |  |  | PAHs | Heavier |
| Control | 0.25 | 59.83 | 0.53 | 15.91 |
| Base | 0.54 | 65.37 | 8.61 | 7.91 |
| EC I | 0.67 | 65.83 | 7.87 | 6.70 |
| EC II | 1.22 | 61.39 | 6.40 | 7.59 |

*weight of oil

TABLE 6

The selected components of the organic liquid fraction from pyrolysis at 400° C. quantified via 2D TOF-MS, with values given as weight percent of organic liquid.

| Compound | BASE | EC I | EC II |
|---|---|---|---|
| 2-methoxy-phenol | 28.91 | 31.55 | 44.88 |
| 1,2-Benzenediol | 9.31 | 9.44 | 12.76 |
| 4-ethyl-2-methoxy-phenol | 5.36 | 5.32 | 7.80 |
| 2-Methoxy-6-methylphenol | 3.75 | 3.89 | 6.32 |
| 2-methoxy-4-(1-propenyl)-phenol | 2.20 | 1.97 | 3.42 |
| Phenol | 1.87 | 2.31 | 2.26 |
| 2-methoxy-4-propyl-phenol | 1.43 | 1.38 | 1.88 |
| Ethanone, 1-(4-hydroxy-3-methoxyphenyl)-phenol | 1.20 | 0.97 | 1.78 |
| 3-methyl-phenol | 1.16 | 1.58 | N/A |
| 2-Methoxy-4-methylphenol | 1.06 | N/A | N/A |

Based on the liquid products that were classified according to components, it is clear that the inventive catalyst blends offer advantages and the different functionalities in the catalyst blend are indeed playing a role in tailoring selectivity. While the PAHs are higher for each catalyst, the heavier components are reduced, indicating that the catalyst blends are capable of preventing these coke precursors. With each catalyst blend the percentage of aromatics increases. Specifically, experimental catalyst II produced nearly 5 times more aromatics than the control, apparently at the expense of phenolic compounds. This shift in product selectivity indicates that the catalyst blend stabilizes monoaromatics during CFP. The yields of pure aromatics are still small compared to the phenolic derivatives that make up the bulk of the liquid product. Table 6 lists the ten most common components of the liquid product and the weight percent of that component for the three catalysts. 2-methoxy-phenol (guaiacol) and 1,2 Benzenediol (catechol) are the two most common phenolic derivatives. These two aromatics are key chemical intermediates in a number of industry value chains. In the case of experimental catalyst II, more than 50% of the total liquid fraction consists of these two components representing a relatively pure product stream from a single process step.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention includes modifications and variations that are within the scope of the appended claims and their equivalents.

The invention claimed is:

1. A catalyst blend for single stage catalytic fast pyrolysis of a feedstock comprising:
   about 40-85 wt % of a zeolite cracking catalyst comprising a mixture of at least one large pore zeolite and at least one intermediate or small pore zeolite in a ratio of 5:1 to 1:5;
   about 4-40 wt % of a heterogeneous transition metal water-gas shift catalyst comprising at least one metal oxide and a support that is optionally promoted; and
   optionally about 3-20 wt % of at least one hydrogenation catalyst.

2. The catalyst blend of claim 1, wherein said at least one large pore zeolite and at least one intermediate or small pore zeolite are selected from the group consisting of FAU, CHA, MOR framework types, ACO, AEI, AEN, AFN, AFT, AFX, ANA, APC, APD, ATT, CDO, DDR, DFT, EAB, EDI, EPI, EM, GIS, GOO, IHW, ITE, ITW, LEV, KFI, MER, MON, NSI, OWE, PAU, PHI, RHO, TH, SAT, SAV, SIV, THO, TSC, UEI, UFI, VNI, YUG, ZON, MFI, LTA, BEA framework types, ZSM-5, ferriente, zeolite Y, zeolite beta, mordenite, MCM-22, ZSM-23, ZSM-57, SUZ-4, EU-1, ZSM-11, (S)AlPO-31, SSZ-23, SAPO, ALPA, and MeALPO.

3. The catalyst blend of claim 2, wherein said at least one large pore zeolite is selected from the group consisting of zeolite Y, and mixtures thereof, and said at least one intermediate or small pore zeolite is selected from the group consisting of CHA, ZSM-5, DDR, and SAPO.

4. The catalyst blend of claim 1, wherein said metal oxide is selected from the group consisting of platinum, rhenium, cobalt, and mixtures thereof, and said support is selected from the group consisting of Al$_2$O$_3$ and silica, and said optional promoter is selected from the group consisting of cerium, molybdenum and tungsten.

5. The catalyst blend of claim 4, wherein said water-gas-shift catalyst comprises platinum (Pt) oxide and rhenium (Re) oxide on a Mo-promoted Al$_2$O$_3$ support.

6. The catalyst blend of claim 1 comprising the at least one hydrogenation catalyst, wherein said at least one hydrogenation catalyst comprises a metal selected from the group consisting of nickel (Ni), copper (Cu), zinc (Zn), and combinations thereof.

7. The catalyst blend of claim 6, wherein said hydrogenation catalyst comprises Ni.

8. The catalyst blend of claim 1, wherein at least one of said cracking catalyst or said hydrogenation catalyst is supported on a solid support.

9. The catalyst blend of claim 8, wherein at least one of said cracking catalyst or said hydrogenation catalyst is supported on porous microspheres.

10. The catalyst blend of claim 9, wherein said porous microspheres are about 70-90 μm in diameter.

11. The catalyst blend of claim 9, wherein said porous microspheres have pores that are about 90-110 nm in diameter.

12. The catalyst blend of claim 9, wherein said cracking catalyst is formed in-situ within pores of said porous microspheres, and said water-gas shift and hydrogenation catalysts are incorporated in or on said microspheres as powders or particles.

13. The catalyst blend of claim 1, wherein the catalyst blend comprises about 50-80 wt % of said cracking catalyst, about 7-20 wt % of said heterogeneous transition metal water-gas shift catalyst, and when present about 7-10 wt % of said hydrogenation catalyst.

14. The catalyst blend of claim 1, wherein said at least one large pore zeolite is zeolite Y, and said at least one intermediate or small pore zeolite is ZSM-5.

15. A catalyst blend for single stage catalytic fast pyrolysis of a feedstock comprising:

a zeolite cracking catalyst comprising a mixture of at least one large pore zeolite and at least one intermediate or small pore zeolite in a ratio of 5:1 to 1:5;
a heterogeneous transition metal water-gas shift catalyst comprising at least one metal oxide and a support that is optionally promoted; and
optionally at least one hydrogenation catalyst; and
wherein:
at least one of said cracking catalyst or said hydrogenation catalyst is supported on a solid support; and
at least one of said cracking catalyst or said hydrogenation catalyst is supported on porous microspheres.

16. The catalyst blend of claim 15, wherein said at least one large pore zeolite is selected from the group consisting of zeolite Y, and mixtures thereof, and said at least one intermediate or small pore zeolite is selected from the group consisting of CHA, ZSM-5, DDR, and SAPO.

17. The catalyst blend of claim 15, wherein said metal oxide is selected from the group consisting of platinum, rhenium, cobalt, and mixtures thereof, and said support is selected from the group consisting of Al$_2$O$_3$ and silica, and said optional promoter is selected from the group consisting of cerium, molybdenum and tungsten.

18. The catalyst blend of claim 15, wherein said water-gas-shift catalyst comprises platinum (Pt) oxide and rhenium (Re) oxide on a Mo-promoted Al$_2$O$_3$ support.

19. The catalyst blend of claim 15 comprising the at least one hydrogenation catalyst, wherein said at least one hydrogenation catalyst comprises a metal selected from the group consisting of nickel (Ni), copper (Cu), zinc (Zn), and combinations thereof.

20. The catalyst blend of claim 15, wherein said porous microspheres are about 70-90 μm in diameter.

21. The catalyst blend of claim 15, wherein the catalyst blend comprises about 50-80 wt % of said cracking catalyst, about 7-20 wt % of said heterogeneous transition metal water-gas shift catalyst, and when present about 7-10 wt % of said hydrogenation catalyst.

* * * * *